United States Patent [19]

Doulakas

[11] Patent Number: 4,829,083

[45] Date of Patent: May 9, 1989

[54] STABILIZATION OF MERCURY-CONTAINING PRESERVATIVES IN OPHTHALMIC MEDICAMENTS

[75] Inventor: Johann Doulakas, Winterthur, Switzerland

[73] Assignee: Dispersa AG, Hettlingen, Switzerland

[21] Appl. No.: 38,315

[22] Filed: Apr. 14, 1987

[30] Foreign Application Priority Data

Apr. 14, 1986 [DE] Fed. Rep. of Germany ....... 3612538

[51] Int. Cl.⁴ .................... A61K 31/34; A61K 31/13
[52] U.S. Cl. .................................. 514/496; 514/669; 514/914; 514/970
[58] Field of Search ............... 514/496, 658, 669, 914, 514/970

[56] References Cited

U.S. PATENT DOCUMENTS

| | | | |
|---|---|---|---|
| 2,958,625 | 11/1960 | Rebold | 167/42 |
| 3,297,524 | 1/1967 | Chodsky et al. | 514/496 |
| 4,518,608 | 5/1985 | Kahan | 514/420 |
| 4,524,063 | 6/1985 | Wheeler | 424/78 |

FOREIGN PATENT DOCUMENTS

| | | |
|---|---|---|
| 58-174310 | 10/1983 | Japan . |
| 58-174309 | 10/1983 | Japan . |
| 1173661 | 12/1969 | United Kingdom . |

OTHER PUBLICATIONS

Dolder et al., Opthalmika, Stuttgart 1983, pp. 401–415.
The Merck Index, Tenth Edition (1983) No. 9575.

*Primary Examiner*—Douglas W. Robinson
*Attorney, Agent, or Firm*—Wenderoth, Lind & Ponack

[57] ABSTRACT

The invention relates to the stabilization of mercury-containing preservatives in liquid or gel-form ophthalmic medicaments. This stabilization against chemical decomposition after the preservative has become deposited on the inner walls of the plastics containers is achieved by adding to the formulation 2-amino-2-hydroxymethyl-1,3-propanediol or a homologue thereof having up to 10 carbon atoms.

2 Claims, No Drawings

STABILIZATION OF MERCURY-CONTAINING PRESERVATIVES IN OPHTHALMIC MEDICAMENTS

The invention relates to the stabilization of mercury-containing preservatives in ophthalmic medicaments, for example eye drops or eye gels, by the addition of 2-amino-2-hydroxymethyl-1,3-propanediol (trometamol) or a homologue thereof having up to 10 carbon atoms. By means of the invention, an increased stability of ophthalmic medicaments incorporating mercury-containing preservatives and an improved tolerability of these preparations in the eye are achieved.

Medicaments for the treatment of eye diseases are often formulated in liquid form and administered in drop form. In the case of eye drops, there is a statutory requirement in most European and other countries that the preparations should be preserved, that is to say protected against attack by micro-organisms and the subsequent multiplication thereof, by adding a component that is capable of preventing or at least checking secondary contamination. In addition, ophthalmic medicaments are often formulated in gel form and the same requirements as regards preservation apply to gels.

Specific mercury-containing substances, for example phenyl mercury borate (merfen) or the sodium salt of 2-(ethylmercurithio)-benzoic acid (thiomersal) have proved to be especially suitable preservatives for use in ophthalmic medicaments.

The mercury-containing preservatives for ophthalmic medicaments have, however, various disadvantages. For example, in the course of time they become deposited on the surface of the inside of the plastics containers in which ophthalmic medicaments are customarily stored. Thus, the content of mercury-containing preservative in small plastics bottles made of low-pressure polyethylene falls to less than approximately 80% of the original content within only a few weeks, and after from 6 months to one year there is practically no mercury-containing preservative, or only a very small amount, in the eye drop or eye gel formulation.

A further disadvantage of mercury-containing preservatives is their poor stability in aqueous solution. For example, thiomersal, which is used especially often owing to its excellent preservative properties, is unstable in aqueous solution The problem underlying the invention is therefore to provide a liquid or gel-form ophthalmic medicament that incorporates a mercury-containing preservative and has outstanding stability for a sufficient period of storage and use. This problem is solved by the surprising finding that stabilization of the mercury-containing preservatives in liquid ophthalmic medicaments can be achieved by adding specific aminopolyols.

The invention therefore relates to an ophthalmic medicament that incorporates a mercury-containing preservative, is to be administered in drop form or gel form and is characterised in that it contains 2-amino-2-hydroxymethyl-1,3-propanediol or a homologue thereof having up to 10 carbon atoms for the stabilization of the preservative.

The invention relates also to the use of 2-amino-2-hydroxymethyl-1,3-propanediol or a homologue thereof having up to 10 carbon atoms for the stabilization of mercury-containing preservatives in ophthalmic medicaments.

2-amino-2-hydroxymethyl-1,3-propanediol, which is known under various names [tromethamine, tris(hydroxymethyl)-aminomethane, tris, THAM, trisamine, tromethane; internationally accepted name trometamol] has the following formula:

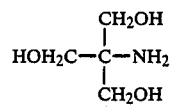

(empirical formula: $C_4H_{11}NO_3$ molecular weight: 121.14)

Trometamol is used as a standard in mass analysis and as a buffer for microbiological and pharmaceutical purposes. It is also used as an emulsifier in cosmetics and as a solution aid in chemistry, especially pharmaceutical chemistry. Furthermore, in medicine it is administered against acidosis in the form of intravenous injections The homologues of 2-amino-2-hydroxymethyl-1,3-propanediol, which can be used for the purposes of the invention, can have up to 10 carbon atoms. These homologous compounds are formed by the introduction of further carbon atoms at one or more positions of the molecular structure shown above. The homologues that have from 5 to 7 carbon atoms are preferred.

Trometamol and its homologues having up to 10, preferably from 5 to 7, carbon atoms can also be illustrated by the following formula:

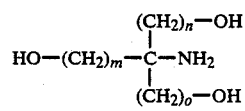

in which m, n and o (independently of one another) each represents an integer of at least 1 and the sum of m, n and o is in the range of from 3 to 9, preferably from 3 to 6.

By the addition of the stabilizer proposed according to the invention, mercury-containing preservatives in liquid or gel-form ophthalmic drugs are stabilized effectively. It has been found that trometamol, or its homologues having up to 10 carbon atoms, prevents the mercury-containing preservatives from becoming deposited on the surfaces of the plastics containers. The mercury-containing preservative remains in solution for several years when the stabiliser proposed according to the invention is added.

The stabilizer proposed according to the invention has the further advantage that it suppresses the tendency of certain mercury-containing preservatives to decompose in aqueous solution. This advantage is demonstrated especially in the case of the preferred preservative thiomersal which is not stable in aqueous solution over a prolonged period. The stabilization is achieved especially by preventing or retarding the adsorption or absorption of the preservative at the inner walls of the plastics containers. By adding trometamol, the chemical decomposition of the thiomersal in the aqueous ophthalmic formulation can be suppressed for a relatively long period so that the preservative is available over the entire period in which the preparation is customarily stored and used. Furthermore, the stabilizer used according to the invention also prevents any cleavage products of thiomersal which may be formed, such as ethylmercury salts, from becoming deposited on the walls of plastics containers.

Surprisingly, it has also been found that the tolerability of specific ophthalmic medicaments in the eye is improved by the addition of the stabilizer proposed according to the invention. This is true, for example, of a recently developed preparation for the treatment of relatively severe acute or chronically recurrent inflammatory symptoms in the eye that contains diclofenac-sodium as non-steroidal anti-inflammatory agent (cf. Example 1 below). In that preparation, which contains thiomersal as preservative, the addition of trometamol results in a distinct improvement in tolerability in the eye.

The stailizer proposed according to the invention is added to the liquid or gel-form ophthalmic medicaments in an amount of from 0.05 to 5%, preferably from 0.1 to 1.0%. In that amount, the stabilizer prevents the mercury-containing preservative from becoming deposited on the inner walls of the plastics containers and thus brings about its desired stabilization. The preservative can therefore act in the desired manner over a relatively long period against attack by micro-organisms and the growth thereof. The preparations can be stored at room temperature and meet the requirements demanded in respect of their storability during therapeutic use.

The ophthalmic medicament may contain any active ingredient suitable for use in the eye, or mixtures of several active ingredients. In addition to the active ingredients mentioned in the Examples there may be mentioned especially: spaglumic acid [N-(N'-acetyl-L-β-aspartyl)-L-glutamic acid] and gentamicin.

The following Examples illustrate the invention:

Example 1

An ophthalmic medicament for the treatment of inflammations that contains diclofenac-sodium as non-steroidal anti-inflammatory agent is manufactured. Thiomersal is used as preservative and trometamol is used as stabilizer. The formulation has the following composition:

| Constituent | Amount |
| --- | --- |
| diclofenac-sodium | 0.1% |
| 2-(ethylmercurithio)-benzoic acid, sodium salt (thiomersal) | 0.004% |
| boric acid | 1.9% |
| trometamol (stabiliser) | 0.6% |
| Cremophor EL ® (reaction product of castor oil and ethylene oxide) (solution aid) | 5.0% |
| water for injection purposes | ad 100% |

This formulation will keep for from 3 to 5 years at room temperature without any significant decrease in the content of preservative being observed over that period.

EXAMPLE 2

| Constituent | Amount |
| --- | --- |
| phenyl mercury (II) dihydrogen borate | 0.020 g |
| trometamol | 0.500 g |
| boric acid | 1.900 g |
| hydroxypropylmethylcellulose | 0.300 g |
| water for injection purposes | 97.980 g |
| | 100.700 g   100 ml |

EXAMPLE 3

| Constituent | Amount |
| --- | --- |
| naphazoline nitrate | 0.005 g |
| zinc sulphate.7 H$_2$O | 0.020 g |
| boric acid | 2.000 g |
| trometamol | 0.100 g |
| witch hazel | 4.000 g |
| orange flower water | 2.000 g |
| lavender water | 6.000 g |
| tincture of euphrasia | 0.080 g |
| phenyl mercury (II) dihydrogen borate | 0.002 g |
| water for injection purposes | 86.093 g |
| | 100.300 g   100 ml |

EXAMPLE 4

| Constituent | Amount |
| --- | --- |
| chloramphenicol | 0.600 g |
| polyethylene glycol 400 | 10.000 g |
| boric acid | 0.900 g |
| trometamol | 0.100 g |
| 2-(ethylmercurithio)-benzoic acid, sodium salt | 0.020 g |
| hydroxypropylmethylcellulose | 0.200 g |
| prednisolone acetate | 0.500 g |
| aluminium hydroxide gel | 1.000 g |
| water for injection purposes | 88.780 g |
| | 102.100 g   100 ml |

The formulations of Examples 2 to 4 have the same long storage life without any significant decrease in the content of preservative as the formulation of Example 1.

I claim:

1. A method of stabilizing mercury-containing preservatives selected from the group consisting of phenyl mercury borate and the sodium salt of 2-(ethylmercurythio)-benzoic acid in eye drops or eye gels which comprises adding to said eye drops or eye gels a compound of the formula

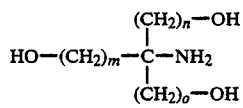

in which m, n and o (independently of one another) each represents an integer of at least 1 and the sum of m, n and o is in the range of from 3 to 9, in an amount of from 0.05 to 5% by weight.

2. A method according to claim 1 wherein the added compound is 2-amino-2-hydroxymethyl-1,3-propanediol.

* * * * *